United States Patent [19]
Stone et al.

[11] Patent Number: 5,819,730
[45] Date of Patent: Oct. 13, 1998

[54] DEVICE FOR ADMINISTERING PHARMACEUTICAL SUBSTANCES

[75] Inventors: Robert Stone; Lynn Michelle Lockett, both of Boronia; Ingo Helmuth Riedel, Victoria; John Ernest Oretti, Doncaster; John Alexander Christie, Wandin, all of Australia

[73] Assignee: Glaxo Wellcome Australia Ltd., Australia

[21] Appl. No.: 549,814

[22] PCT Filed: Jun. 9, 1993

[86] PCT No.: PCT/EP94/01859

§ 371 Date: Jun. 19, 1996

§ 102(e) Date: Jun. 19, 1996

[87] PCT Pub. No.: WO94/28956

PCT Pub. Date: Dec. 22, 1994

[30] Foreign Application Priority Data

Jun. 9, 1993 [GB] United Kingdom ............... 9311892

[51] Int. Cl.⁶ ............... A61M 15/00; B05B 17/06
[52] U.S. Cl. ............... 128/203.21; 128/200.14; 128/200.22; 128/200.23; 128/205.16
[58] Field of Search ............... 128/200.22, 200.23, 128/200.21, 203.22, 200.14, 205.13, 205.14, 205.15, 205.16, 205.18, 203.15, 203.23; 604/37, 38, 214; 222/162, 160, 213, 173, 206, 153; 239/102.2, 327, 321, 338

[56] References Cited

U.S. PATENT DOCUMENTS

| | | | |
|---|---|---|---|
| 2,442,004 | 5/1948 | Haywood et al. | 128/203.21 |
| 2,696,211 | 1/1954 | O'Gatty | 128/205 |
| 2,705,007 | 3/1955 | Gerber | 128/203.21 |
| 3,024,947 | 3/1962 | Jeynes, Jr. | 222/80 |
| 3,425,414 | 2/1969 | Roche | 128/203.21 |
| 3,856,142 | 12/1974 | Vassalo | 128/200.23 |
| 4,095,596 | 6/1978 | Grayson | 128/198 |
| 4,137,914 | 2/1979 | Wetterlin | 128/203.23 |
| 4,177,939 | 12/1979 | Thomas | 222/153 |
| 4,454,877 | 6/1984 | Miller et al. | 128/200.23 |
| 4,771,769 | 9/1988 | Hegemann | 128/200.22 |
| 4,801,093 | 1/1989 | Brunet et al. | 239/490 |
| 4,860,740 | 8/1989 | Kirk et al. | 128/203.15 |
| 4,898,166 | 2/1990 | Rose et al. | 128/205.1 X |
| 4,962,868 | 10/1990 | Borchard | 222/49 |
| 5,031,800 | 7/1991 | Brunet | 222/153 |
| 5,035,348 | 7/1991 | Seifert | 222/107 |

FOREIGN PATENT DOCUMENTS

| | | |
|---|---|---|
| 87184/75 | 6/1977 | Australia . |
| 1005261A6 | 6/1993 | Belgium . |
| 2 020 425 | 1/1991 | Canada . |

(List continued on next page.)

*Primary Examiner*—John G. Weiss
*Assistant Examiner*—V. Srivastava
*Attorney, Agent, or Firm*—Bacon & Thomas

[57] ABSTRACT

The present invention relates to a device for administering pharmaceutical substances by spraying the contents of a container formed of plastics material. The device comprises a pair of members between which is supported the container, the members being movable relative to each other between a first position in which the container is not compressed sufficiently to burst it and a second position in which the members are capable of exerting sufficient pressure on the container to burst it and expel the contents through a discharge outlet.

24 Claims, 16 Drawing Sheets

FOREIGN PATENT DOCUMENTS

| | | |
|---|---|---|
| 0 282 338 | 9/1988 | European Pat. Off. . |
| 0 407 276 | 1/1991 | European Pat. Off. . |
| 0 452 728 | 10/1991 | European Pat. Off. . |
| 0 469 814 | 2/1992 | European Pat. Off. . |
| 0 557 714 | 9/1993 | European Pat. Off. . |
| 0557714 | 9/1993 | European Pat. Off. ............... 239/327 |
| 0 580 897 | 2/1994 | European Pat. Off. . |
| A-1 413 975 | 9/1965 | France ......................... A61M 11/00 |
| 2 516 387 | 5/1983 | France . |
| 2692175 | 12/1993 | France .................................. 239/338 |
| 518 744 | 3/1970 | Switzerland . |
| 90/00496 | 1/1990 | WIPO . |
| 90/14893 | 12/1990 | WIPO . |
| 91/12197 | 8/1991 | WIPO . |
| 91/12198 | 8/1991 | WIPO . |
| 92/20455 | 11/1992 | WIPO . |
| 93/02804 | 2/1993 | WIPO . |
| 93/10015 | 5/1993 | WIPO . |
| 93/10422 | 5/1993 | WIPO . |
| 93/10852 | 6/1993 | WIPO . |
| 93/19806 | 10/1993 | WIPO . |
| 9409912 | 5/1994 | WIPO ................................. 239/102.2 |

FIG. 3
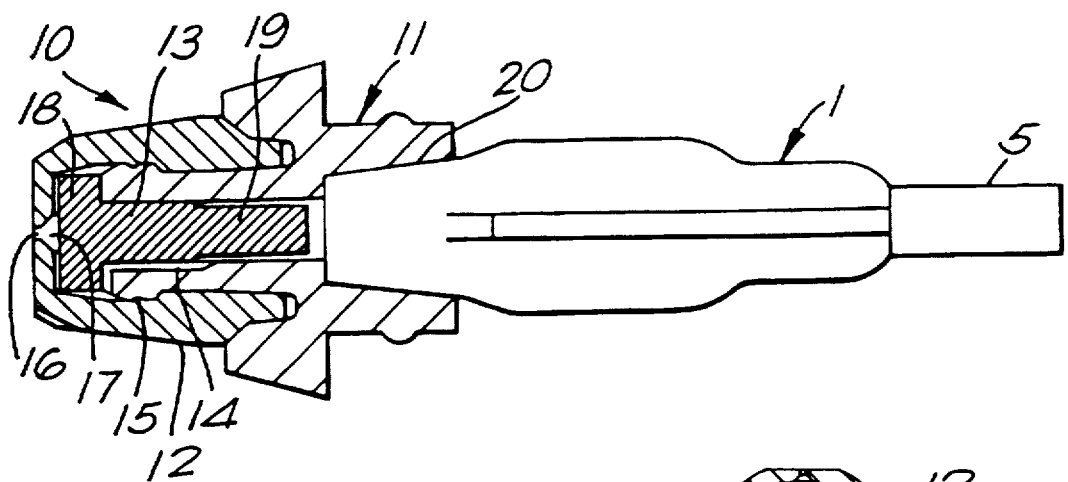
FIG. 4a
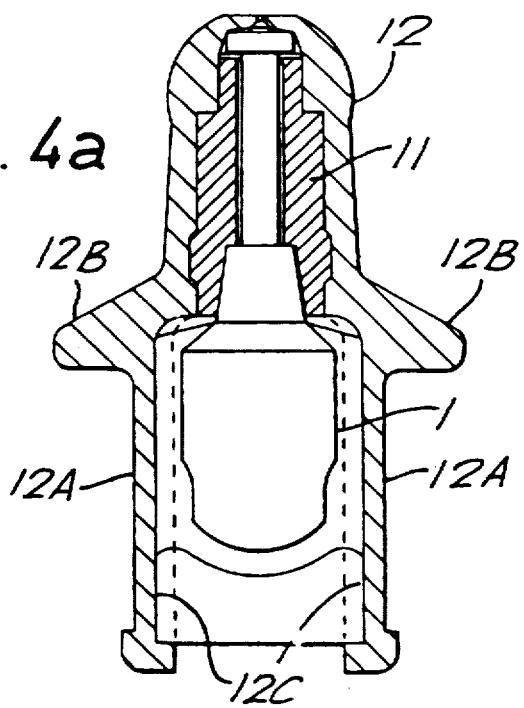
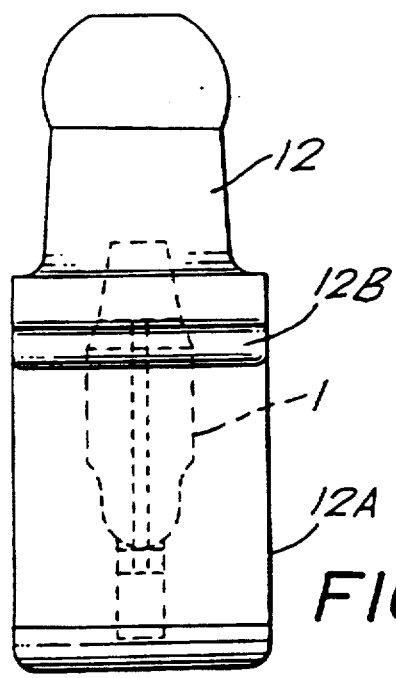
FIG. 4b

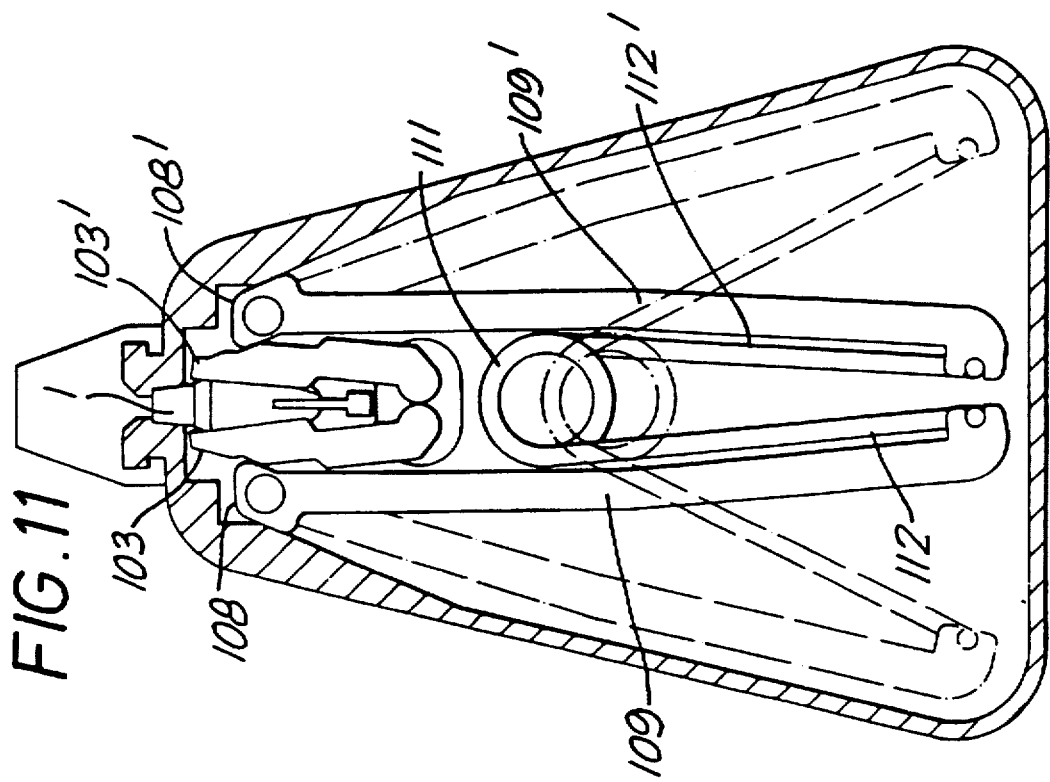
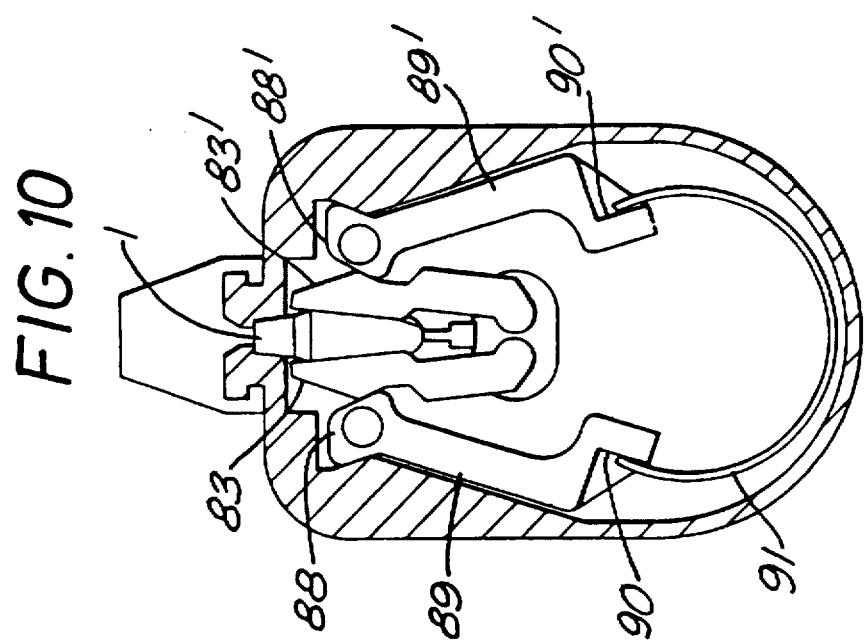
FIG. 10
FIG. 11

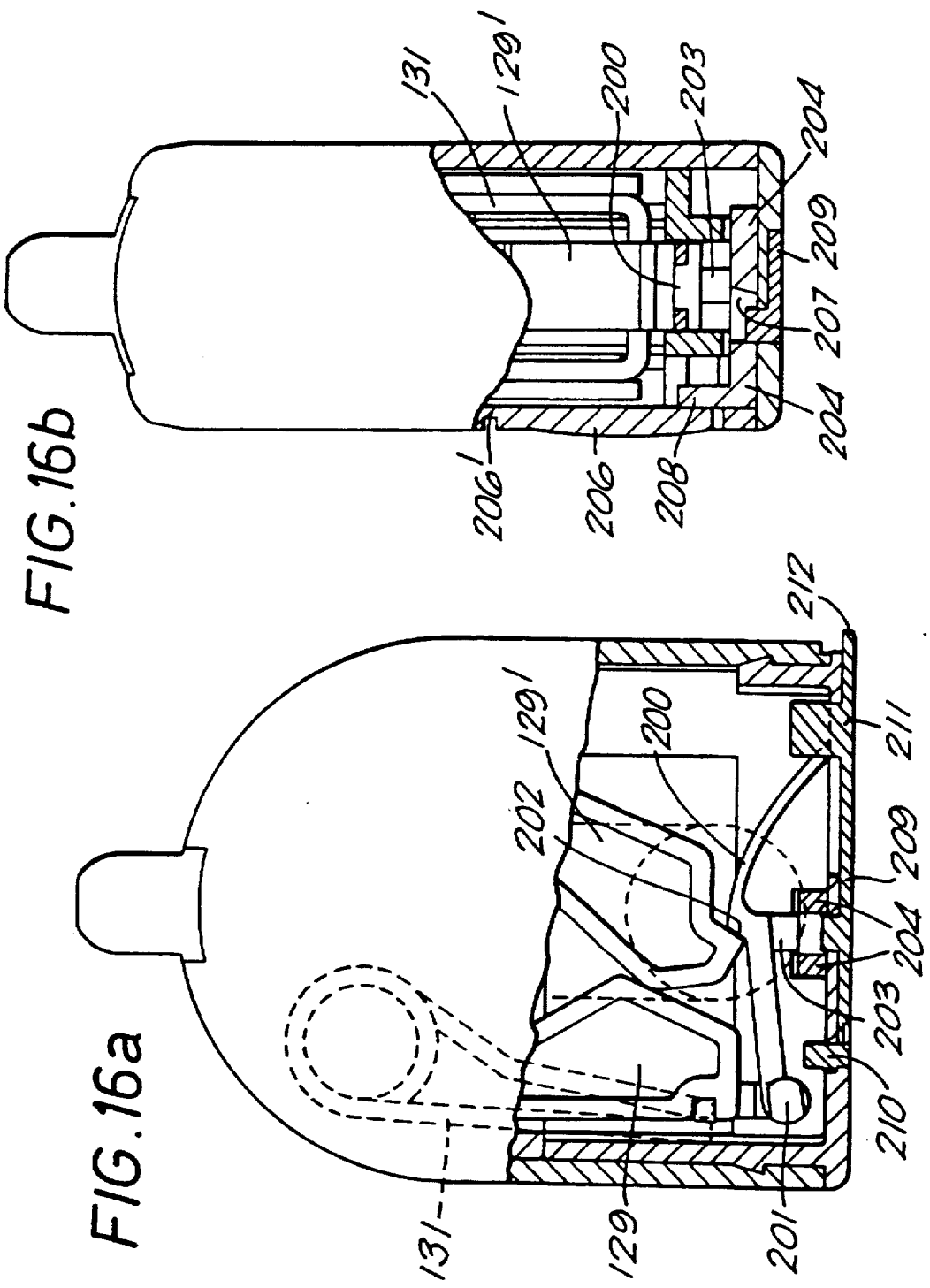

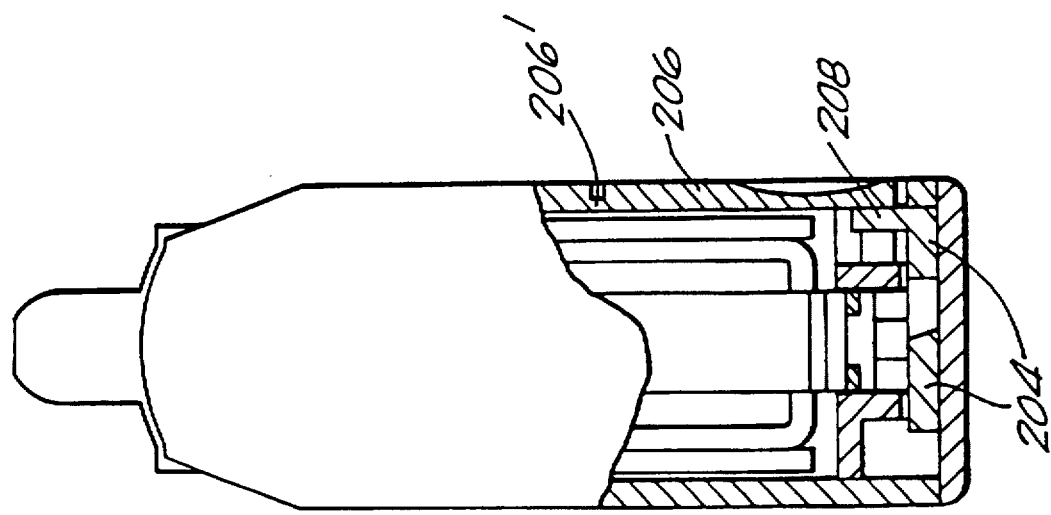
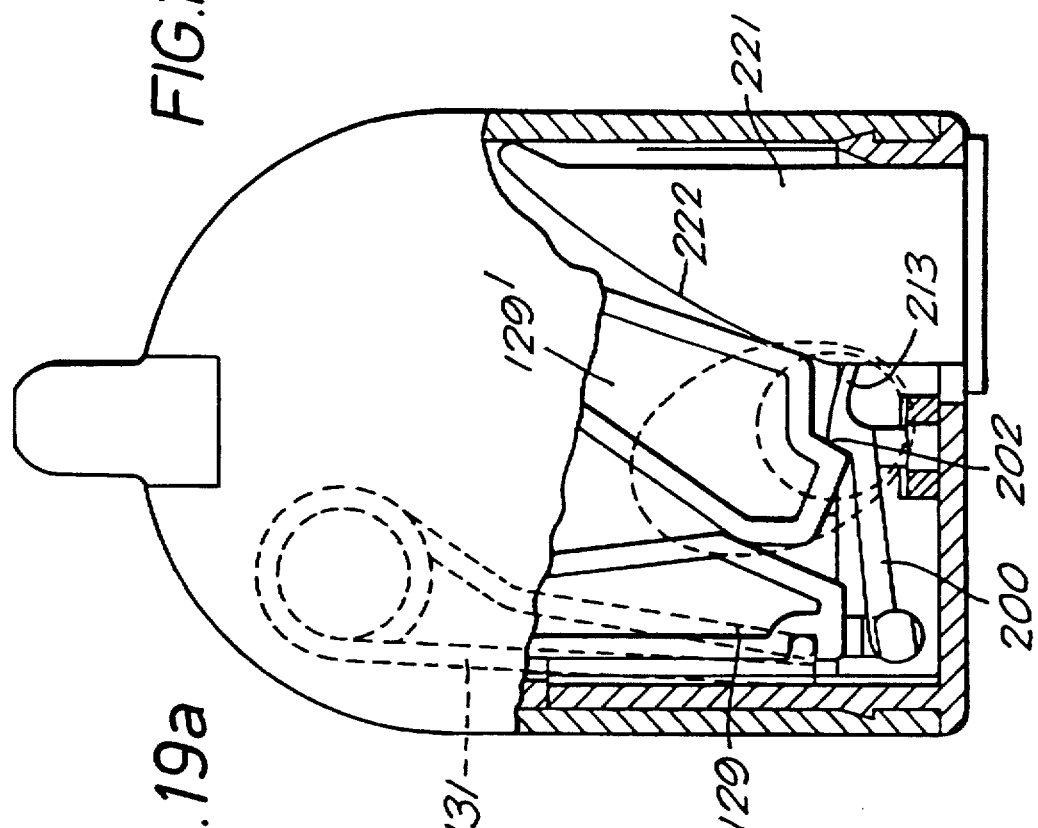

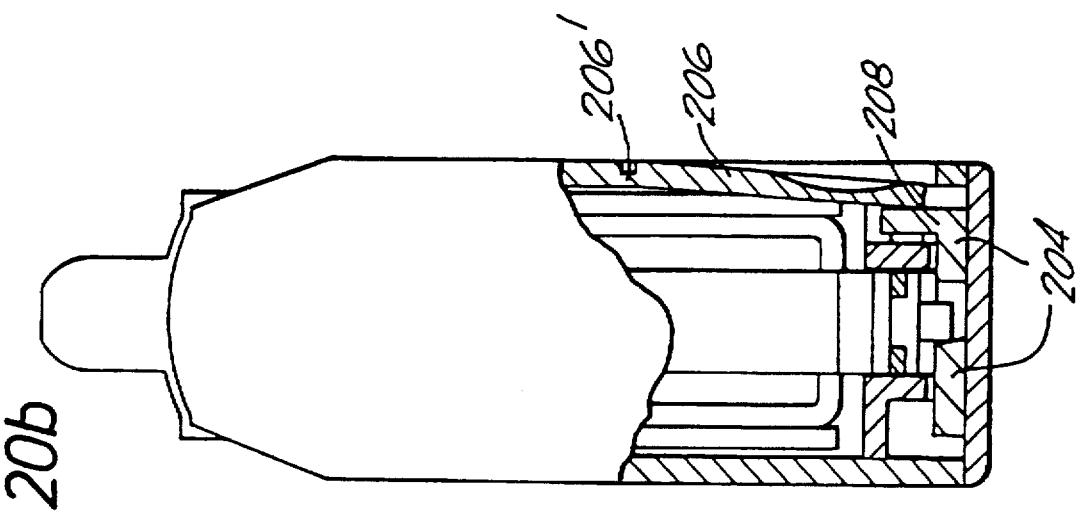
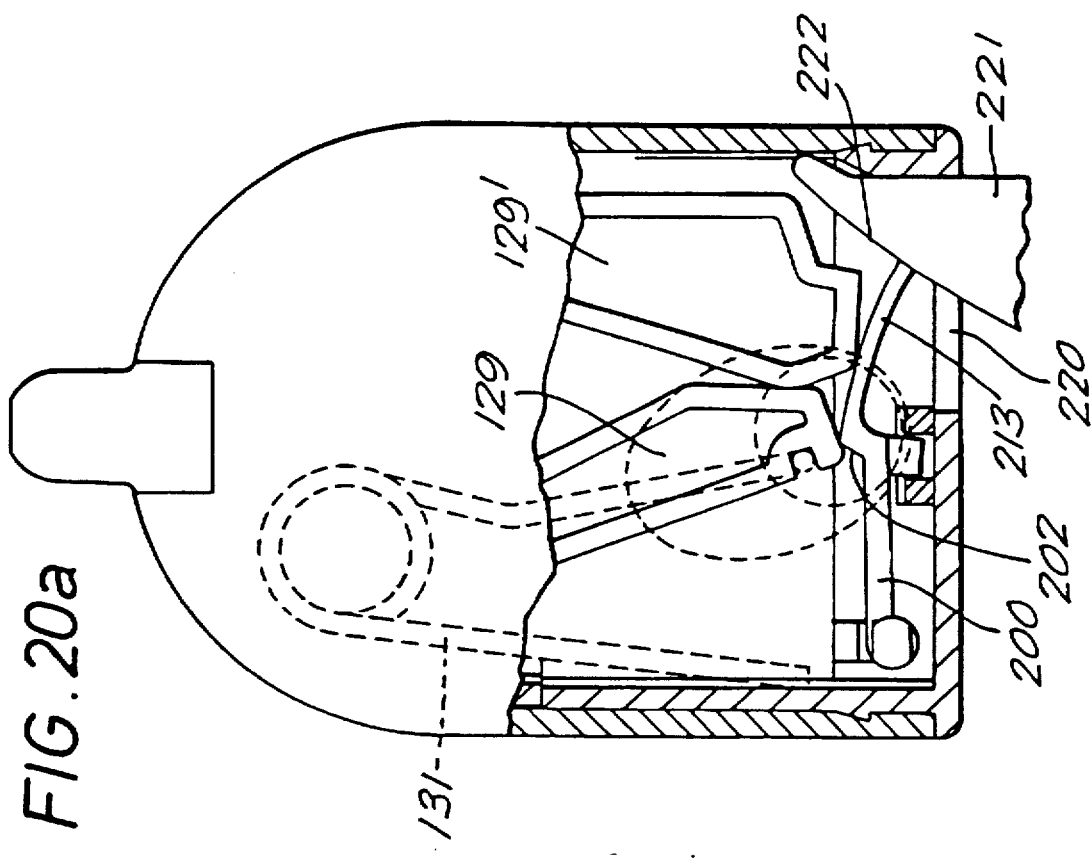

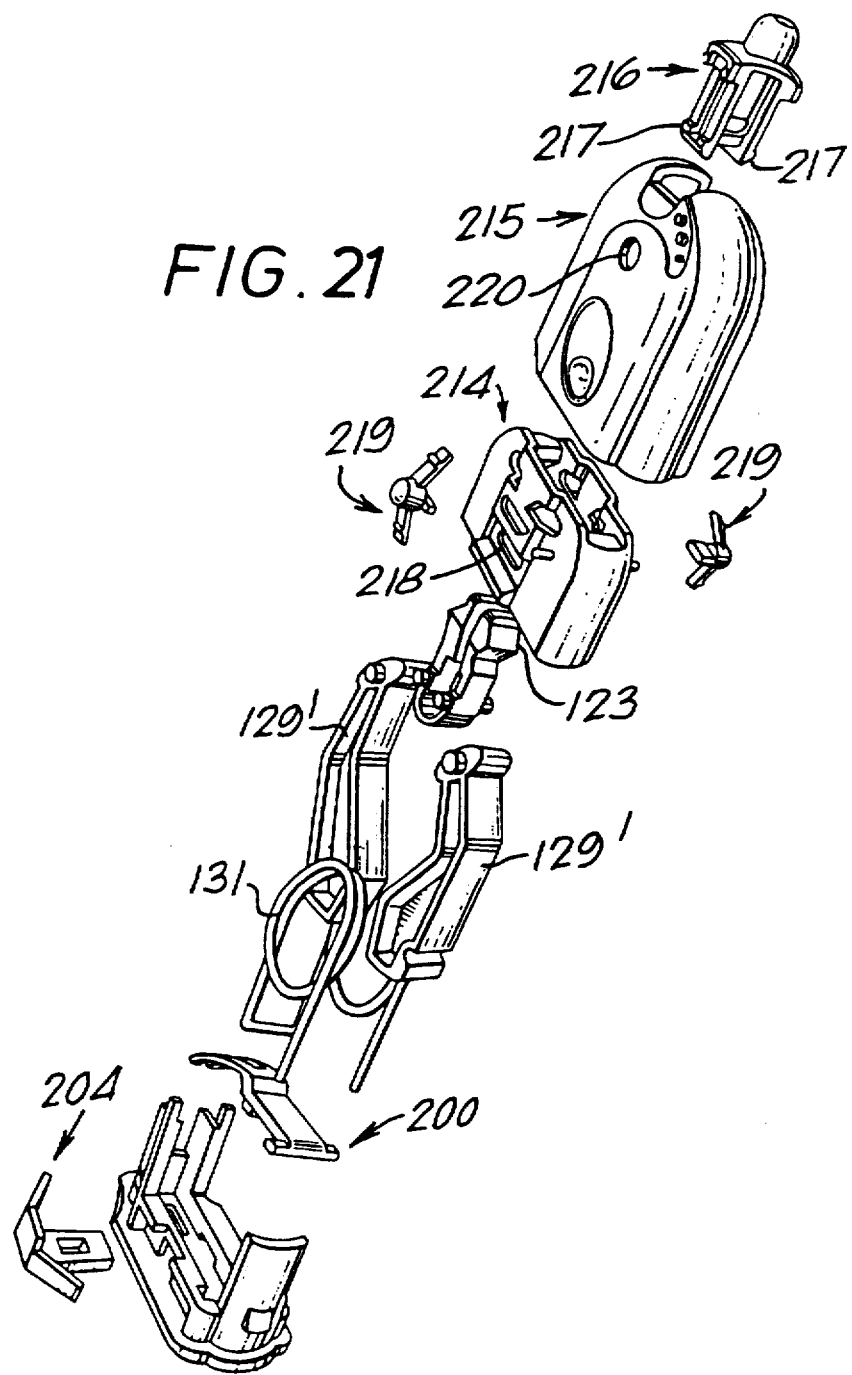

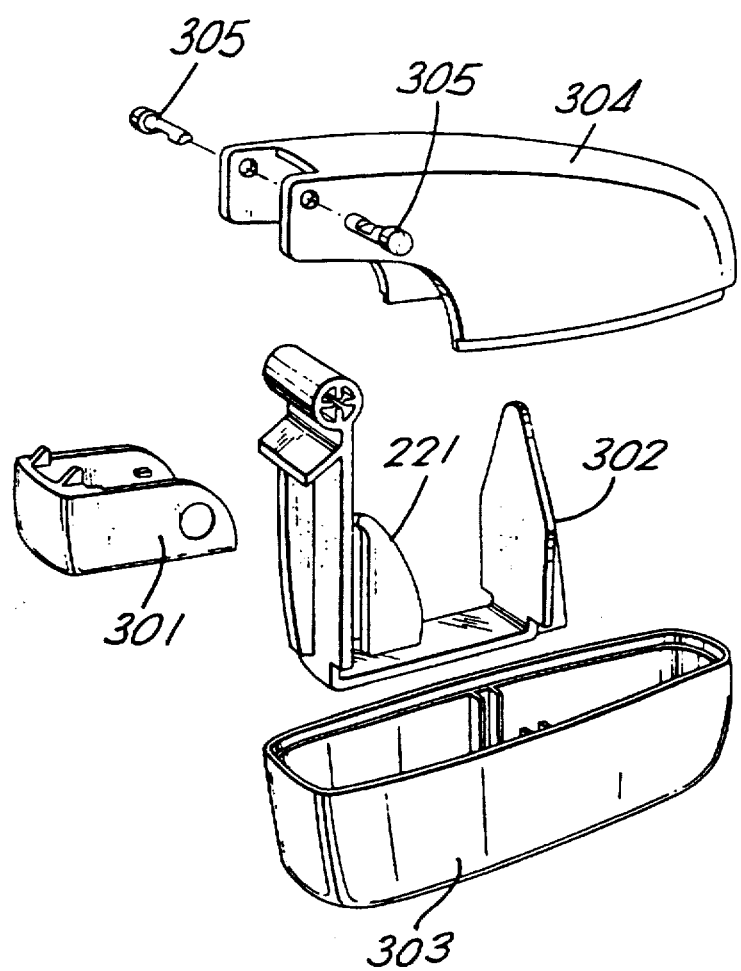

DEVICE FOR ADMINISTERING PHARMACEUTICAL SUBSTANCES

The present invention relates to a device for administering pharmaceutical substances. The device delivers the pharmaceutical by means of a spraying action and is particularly adapted for intranasal administration of a predetermined dose of a pharmaceutical substance.

Devices for administering pharmaceutical substances by spraying are known, for example ones using aerosol canisters for treatment of asthma. In a different medical area, it is known to use capsules of pharmaceutical substances which can be cut or squeezed open to pour the contents onto a cloth or into water, for example to relieve blocked nasal passages. Such capsules are formed of plastics material. Nasal sprays are also well known, in which a container is placed at a nasal cavity and squeezed by hand, thereby spraying the contents out through a nozzle.

International patent publication No. WO88/02266 discloses a container for delivery of a liquid medicine, in particular for intranasal delivery. The container body has a squeezable chamber filled with air and a chamber filled with the medicine, the two chambers being separated by a wall with a one-way valve formed therein. Upon removal of a cap, the medicine can be delivered through an orifice in the second chamber by squeezing the first chamber between the user's finger and thumb.

UK patent application No. 2255918 discloses a dispensing device comprising a magazine of cartridges full of a fluid to be atomised. The cartridges are fed in turn to a space below a spring-loaded plunger. On actuation, the plunger impacts upon the cartridge to pressurize the contents and eject them through atomising means which form part of the cartridge. The atomising orifice can be covered with a thin layer of plastic film or wax which ruptures at use or is removed prior to use. In an alternative arrangement, cartridges are inserted into the device one at a time, eliminating the need for a magazine holder.

U.S. Pat. No. 4,961,727 also describes a device for delivering a medicine to the nasal cavities. The device consists of a flexible-walled container having a discharge head with a swirl chamber and a dip-tube depending from the swirl chamber into the container. In use, the container is squeezed by hand to drive liquid up the dip-tube and into the swirl chamber to be discharged into the nasal cavity in a "fountain" of relatively large droplets. The container can include a capsule of a medicinal product which is ruptured by squeezing of the container, the product then being mixed with the liquid in the container.

The present invention aims to provide a new device which is simple to use and is particularly adapted for administering medicaments to the nasal passages or respiratory tract. It will be appreciated by those skilled in the art that to be effective medicaments administered to the nasal cavities or respiratory tract are required to be delivered in a form in which they can be readily absorbed or otherwise reach the site of action of the medicaments. In general such medicaments are administered to the nasal cavities in a liquid carrier, the medicament being in the form of a solution or suspension in a pharmaceutically acceptable vehicle. The preferred means of administration is by presenting the liquid as a spray. It is further desirable that the medicament is maintained in a sterile form until use. Preferably a predetermined dose of a pharmaceutical substance is delivered to the nasal passages or respiratory tract.

The invention provides in a first aspect a device suitable for administering pharmaceutical substances by spraying the contents of a container formed of plastics material, the device comprising a pair of members for supporting the container, and a discharge outlet, wherein when the container is present one or both members are movable between a first position in which the container is not compressed sufficiently to burst it and a second position in which the members are capable of exerting sufficient pressure on the container to burst it, thereby expelling the contents through the discharge outlet.

The invention provides in a further aspect a combination of a device as defined above and a plastics container, the container having a predetermined point of rupture. Preferably the container will also rupture at a pre-determined pressure.

The first and second members may cooperate through any means which permit the application of sufficient pressure to the container to rupture the container. The two members are preferably pivotally moveable relative to each other.

The container can be held between the first and second members so that when the members are squeezed together by the user (for example by the user's hand) the container is pressed until it ruptures. After rupture, the members will tend to continue to travel until the contents are expelled through the discharge outlet. It will be appreciated that where the two members are pivotally moveable the force applied to the container will be determined by the force applied by the user and the lever arm. Alternatively or additionally means for magnifying the force employed by the user may be incorporated into the device.

One such means for magnifying the force is a cam mechanism interposed between the one or both movable members and one or a pair of separate handle members.

The discharge outlet and the movable member may be in any convenient orientation with respect to one another. Conveniently the direction of discharge of the medicament will be generally parallel to the movable members.

Preferably the device will be such that the force applied by the user will be relatively constant for different users and on each occasion a single user employs the device. For example, the device may be provided with means which prevent actuation until a pre-determined pressure has been applied, such as a breakable plastic tab. Alternatively, a spring can be provided in the device which urges the members supporting the container together upon release of the spring force by a trigger mechanism.

The discharge outlet can be a simple element which merely ensures that the spray from the burst container is channelled in the right direction, or it can be a more complex element which modifies the spray from the ruptured container, thereby attaining a more desirable spray pattern. The desirability of having a predetermined spray pattern depends to a large extent on the particular pharmaceutical being dispensed and the site of deposition and action and the part of the body into or onto which it is being sprayed.

The spray pattern desired for administration to the nasal passages may comprise relatively large droplets. Where administration to the respiratory tract is required smaller droplets are preferred. The appropriate spray pattern will be apparent to those skilled in the art.

The provision of a desired spray pattern is determined inter alia by the velocity at which the medicament is discharged from the container; the velocity is dependent upon the pressure generated in the sealed container which is itself determined by the force applied to the container by the or each movable member. Suitable pressures will be apparent to those skilled in the art.

The fact that, in the invention, a container with a known volume of medicament therein is used means that a given dose can be reliably administered. Furthermore, since the pressing action on the container is performed via mechanical means, rather than simply between finger and thumb, the discharge from the container is more predictable and uniform.

A predetermined point of rupture in the container may be provided by any convenient means known in the art. Preferably the point of rupture will comprise an area of reduced thickness in comparison to the walls of the container.

The use of a single container, delivering a "unit dose", also enables sterility to be maintained, which is vital in certain applications. The entire device can be disposable or a supply of units comprising the container and the discharge outlet can be provided for use in a reloadable device.

In one aspect of the invention the device is provided together with a housing for the device and at least one container of the pharmaceutical substance to be discharged. Preferably the housing has a lid which may be closed after the device is returned thereto. The housing may include means to prime the spring and trigger mechanism when the device is placed into the housing.

The pharmaceutical substance inside the container can be a liquid or suspension preparation. It will be appreciated by those skilled in the art that the medicaments in liquid form will require a relatively low viscosity for effective administration as a spray with the device of the invention. In practice it has been found that liquid formulations with a viscosity of about 1 to about 100 centistokes are appropriate.

The device of the invention can be used for the following, non-exclusive, applications:

intranasal delivery of drugs for systemic or local effect, topical delivery of drugs for local treatment of burns, wounds etc;

delivery of drugs to the oral cavity for local treatment, e.g. for use prior to or after dental surgery, for treatment of mouth ulcers, or for treatment of throat infections etc;

delivery of drugs to the peritoneal or other body cavities exposed during surgical procedures.

delivery to the lungs and other parts of the respiratory tract for systemic or local effect.

The invention also provides a method of administering pharmaceutical substances by spraying the contents of a container formed of plastics material by applying sufficient pressure to the container to burst it and expel the contents through a discharge outlet.

Preferred embodiments of the invention are described in detail below, by example only, with reference to the accompanying drawings, wherein:

FIG. 3 is a sectional view of a nozzle to be used as a discharge outlet in the administering device of the invention;

FIG. 4a and 4b are sectional and elevation views, taken at right angles to one another, of a container/nozzle unit;

FIG. 10 is a sectional view of a fourth embodiment of an administering device according to the invention;

FIG. 11 is a sectional view of a fifth embodiment of an administering device according to the invention;

FIGS. 16a, 16b, 17a and 17b are detailed sectional views of a seventh embodiment of an administering device, the views showing another trigger mechanism together with a safety mechanism preventing accidental actuation;

FIGS. 19a, 19b, 20a and 20b are detailed sectional views of an eighth embodiment of an administering device, similar to that of FIGS. 16 and 17, but including a repriming mechanism:

FIG. 21 is a perspective exploded view of the embodiment shown in FIGS. 19 and 20; and FIG. 22 is a perspective exploded view of a carry case for use with the administering device shown in FIGS. 19 and 20.

A complete administering device which is ready for use consists of three components: the container for the substance to be dispensed; a discharge outlet for directing the contents of the container to the desired treatment site; and the actuator which is used by the patient to burst the container and discharge the contents thereof. These three components are described in turn below.

1. THE CONTAINER

Figure 1:
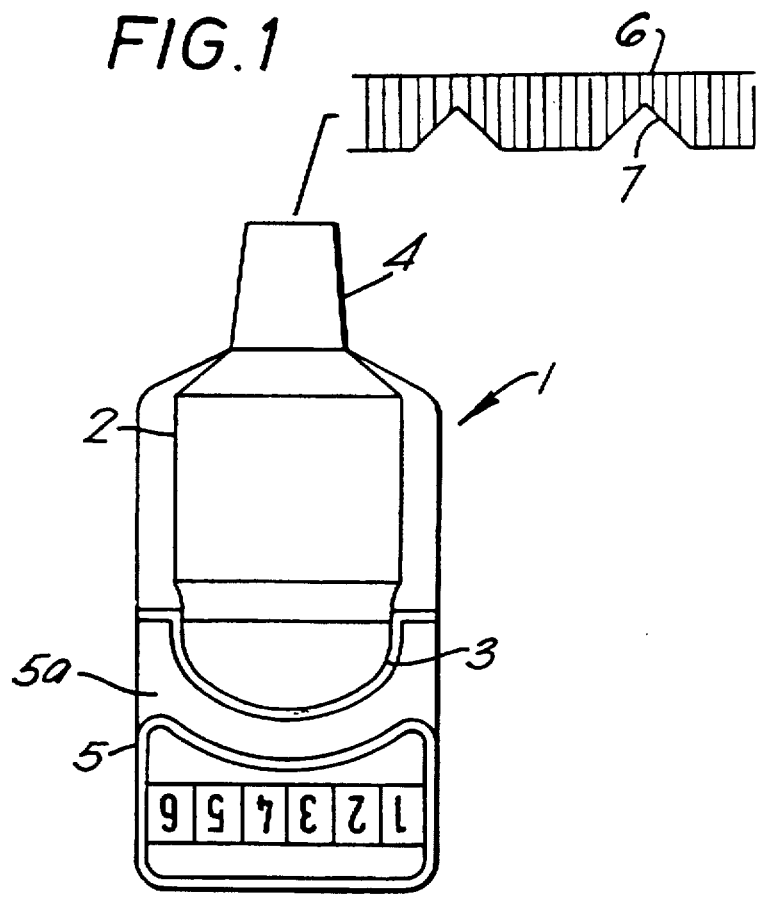
FIG. 1 is an elevational view of a container to be used in an administering device according to the invention.

An example of a suitable container is shown in FIG. 1. The container 1 consists of a rounded, hollow body portion 2, a curved base portion 3 and a tapered neck portion 4. Extending from two opposite sides of the body portion and from the base portion is a substantially planar tab portion 5. The purpose of forming this tab portion is discussed in more detail below.

At the outer end of the neck portion of the container is formed a rupturable wall or membrane 6. This may be formed by a predetermined area of the end face of the container having a thickness which is substantially less than the other walls of the container or can be formed, as illustrated in the enlarged detail of FIG. 1, by a circular line of weakness 7.

The important point about the rupturable part of the container is that it is so formed that it will always rupture before any other part of the container when a given force is applied to the container.

The container can be formed by the "fill and seal" moulding method. In this method, details of which are well known in the art, the bottle is moulded upside down, that is the neck and body portions are moulded first, the container is then filled with the desired substance in liquid form, and lastly the base portion is moulded on top, thus sealing in the contents of the container.

This moulding method may be substantially as described in U.S. Pat. Nos. 4,178,976 and 4,176,153 (Automatic Liquid Packaging, Inc.), the disclosure of these patents being incorporated herein by reference.

The circular line of weakness 7 seen in FIG. 1 may be formed in the moulding process by means of the tip of the filling nozzle. This can be pressed into the end wall of the neck portion 4 to form a ring of reduced thickness in the moulding process. The filling nozzle is then retracted to fill a container in the usual way. After the filling is complete, the nozzle is fully retracted to allow the sealing mould to move across and seal the container.

Figure 2:
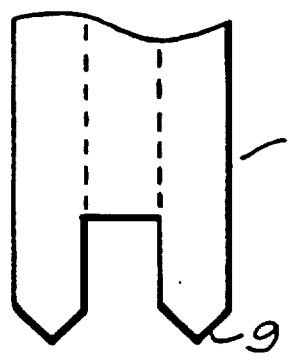
FIG. 2 is a detail view illustrating a part for use in the forming process of the container.

An example of the shape of the tip of the filling nozzle is seen in FIG. 2. The nozzle pin 8 is cylindrical, with a diameter of approximately 1.5 mm and a central bore through which the container is filled. The diameter of the central bore is reduced to typically 0.5 mm to provide adequate control for accuracy of filling. The annular rim 9 is doubly bevelled to form a circular, sharp ridge.

Other nozzle pin designs can be used. Furthermore, the circular line of weakness or the membrane on the container could be formed by a pin separate from the filling nozzle. In this case, the pin obviously does not need to be hollow.

The points of connection between the base portion 3 and the body portion 2 which are formed when the container is closed are potential areas of weakness. Since it is critical that the container, when compressed, ruptures at the neck end, it is preferable for the sealing mould to form the tab portion 5 at the same time as it seals the container. The part 5a of the tab portion at the end of the container, and also along the sides, provides structural support to the container to ensure that the weakest point is at the end of the neck portion.

The surface of the tab can also be used to give information on the contents of the container and also an expiry date for the contents, for example.

The body portion 2 of the container may be circular or oval in cross section. The neck portion 4 may be tapered, as illustrated, or may be cylindrical. The wall thickness of the container may be from 0.3 to 0.7 mm. The thickness of the line of weakness or the thickness of the rupturable membrane might be 0.05 to 0.2 mm. The volume of the container might be from 0.05 to 2.0 ml, preferably 0.1 to 1.0 ml; for intranasal administration, the volume is preferably 0.1 to 0.15 ml.

The container can be moulded from any suitable plastics material, for example LDPE (low density polyethylene).

The container must obviously burst at a level of pressure which can easily be produced in the container by means of the actuating device (examples of which are described later). Furthermore, the pressure must be high enough to expel the contents of the container out of the actuator through the discharge outlet. It has been found that forces applied to the containers of from about 10 to about 100 kgf, for example about 15 to about 60 kgf, in particular about 15 to about 35 kgf, are sufficient to achieve the desired velocity and the spray pattern of the medicament for administration to the nasal passages.

2. THE DISCHARGE OUTLET

As previously indicated, the discharge outlet can either be an open channel which directs the contents of the container, upon bursting, to the desired point of application or can be a nozzle device which modifies the flow of the contents as it is expelled from the container. Generally speaking, if a solution in the container is of a high viscosity, it will need to be delivered along an open channel, whereas it will generally be desirable to control the flow of low viscosity liquids. Control of the flow of a low viscosity liquid is particularly important where the substance in the container is being administered intranasally or to the respiratory tract. A predetermined spray pattern is desirable for efficient administration, along with predetermined particle size. The preferred particle size range for intranasal application is 10 to 50 μm. Where the administration is to the respiratory tract, the preferred particle size is less than 10 μm.

An example of a suitable nozzle is illustrated in FIG. 3. This nozzle is substantially as described in International Patent Publication No. WO92/01919 (Australian Biomedical Corporation Limited). This nozzle is used to change the direction of flow of fluid along the nozzle bore to create a generally concentric fluid flow, by means of a swirl chamber.

The nozzle 10 includes a main body 11, an end cap 12 and a nozzle plug 13. The main body 11 has flow splitting channels 14. End cap 12 has an internal circumferential lip 15 which seals with the main body 11. The cap has an axially located exit orifice 16, behind which is a swirl chamber 17. A structure 18 acts to direct fluid into the swirl chamber 17 to ensure that the flow is concentric to the chamber axis. The nozzle plug 13 has a spigot 19. The nozzle shown in the Figure achieves a small vortex spray chamber effect whereby fluid is forced under pressure into the circular swirl chamber 17 in such a manner that the flow is concentric to the axis. The spray exits through central outlet 16.

The spray nozzle body 11 is formed with an internally tapered seat 20 whose dimensions are matched to those of the neck portion of the container described above. It is important that there should be a tight connection between the container and the nozzle so that no leakage occurs. This ensures that all the contents expelled from the container are efficiently delivered to the nozzle.

The container 1 can be connected to the nozzle 10 by means of a push-fit, or possibly by means of a screw fit (not illustrated).

It is also desirable that there be a minimum of spare volume between the container and the nozzle in order that there is no significant loss of pressure on transfer of the contents of the container to the nozzle and for efficient and reproducible delivery of the contents. In the nozzle illustrated, it will be seen that the container is fitted with the end of the neck portion immediately communicating with the outlet channels 14 of the nozzle.

It will be appreciated that if the complete administering device is a disposable unit, to be discarded by the user after one operation, then the nozzle can be an integral part of the actuator (to be described below). If the actuator is, on the other hand, to be reusable, then a supply of combined container/nozzle units will be supplied to the user to be loaded into the actuating device.

Another example of a combined container/nozzle unit is shown in FIGS. 4a and 4b. In this unit, the end cap 12 encapsulates the main body 11 and extends downwardly to form a pair of parallel flat legs 12A beneath shoulders 12B. On the inside of each lug 12A is a longitudinal slot 12C.

The container 1 can be fitted into the cap 12 by separating the legs 12A and clipping the sides of the container into the slots 12C. The container is thus accessible from two sides, between the legs 12A.

This container/nozzle unit can be used in conjunction with the actuators described below, in particular those illustrated in FIGS. 11 to 21. The unit snaps inside those actuators which are intended to be disposable, and cannot be dislodged, whereas for actuators which are intended to be reusable, the unit is removable to allow a fresh unit to be fitted.

3. THE ACTUATOR

The function of the actuator is to support the container in a position in which it can then be compressed in order to be ruptured and its contents expelled through the discharge channel or nozzle fitted in the actuator. The container can either be supported on a first member and a second member be moveable relative to the container to compress it, or the container can be supported between two members, each of which moves relative to the container, towards the other member, in order to compress the container. It is convenient to think of the two types of actuator as having either one movable member or two movable members, though obviously, in order to compress the container, each of the two members is always movable relative to the other member.

The actuators described below can be characterised in two different ways. Firstly, the actuators are either purely manually operated or are operated by means of some integral energy store, in particular a spring; the latter type are socalled "stored energy" devices. Secondly, the actuators are either intended to be disposable, i.e. discarded after a single use, or are intended to be reusable, i.e. a fresh container and/or container/nozzle unit is to be inserted after each use.

The actuators of FIGS. 5 to 9 are manual devices. The actuators of FIGS. 10 to 21 are stored energy devices. The actuators of FIGS. 5 to 8, 10 and 14 to 18 are intended to be disposable. The actuators of FIGS. 9, 11, 12 and 19 to 21 are intended to be reusable. The different features of the different types of actuators will become apparent from the detailed description which follows.

Figure 6:
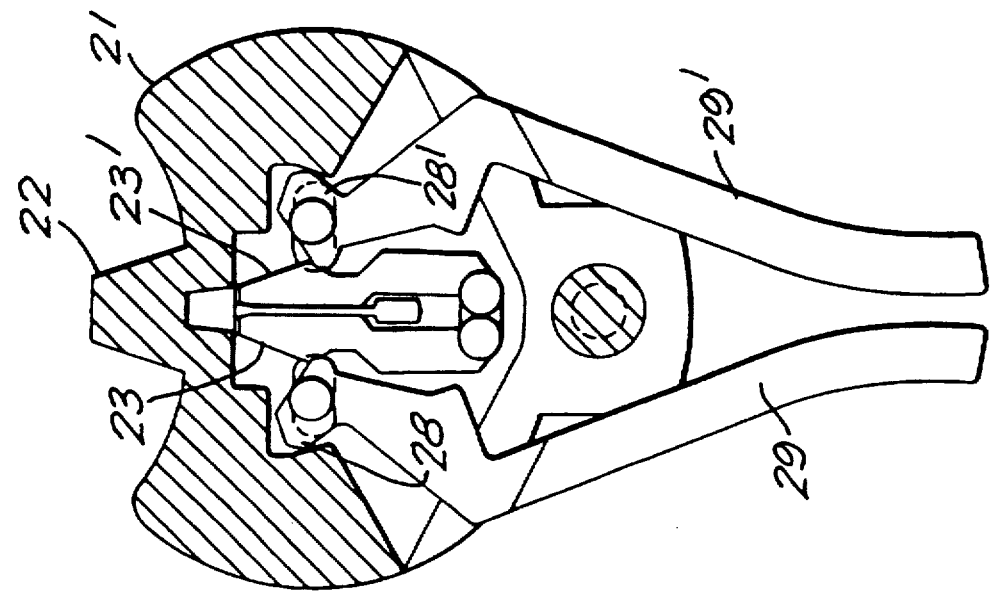
FIGS. 5 and 6 are sectional views of a first embodiment of the administering device according to the invention showing the device prior to discharge of the contents of the container and after discharge respectively.
Figure 5:
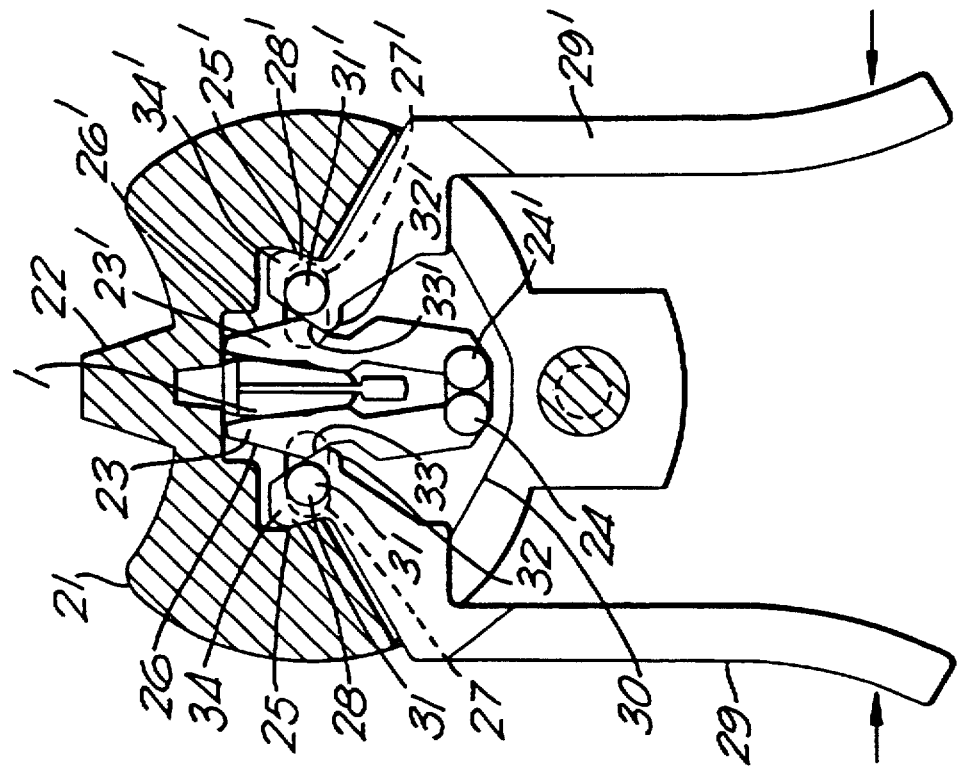

The actuator as shown in FIGS. 5 and 6 comprises a head portion 21 which is substantially circular in elevation, with a segment removed from its upper part and a nozzle portion formed in that segment. The nozzle 10 which is described above is not shown in any detail in FIGS. 5 and 6.

The head portion 21 is hollow and mounted within the cavity of the head portion 21 is a pair of movable members 23, 23' between which is supported the container 1. The movable members 23, 23' form a pair of jaws, each of which is pivoted at a point 24, 24' remote from the nozzle portion 22 of the head, the two pivot points 24, 24' of the jaw members being adjacent. It is not essential that the two jaw members have separate pivot points; they could share a common pivot point.

The cavity of the head portion has, on either side of the pair of jaw members, shoulders 25, 25' so that a gap is defined between the inner wall of the head portion 21 and the outer surface 26, 26' of each jaw member.

The outer wall of the head portion 21, adjacent each gap, is formed with a slot 27, 27' which extends in a direction substantially perpendicular to the faces of the jaw members 23, 23'. Fitted into each gap is the head 28, 28' of an arm 29, 29', the arm extending through an opening 30 in the base of the head portion 21 to define handle means for gripping by the user. The pair of arms 29, 29' thus form a pair of handles which can be squeezed in the manner of a pair of pliers or the like.

Each head 28, 28' of each arm has a lug 31, 31' which fits into the corresponding slot 27, 27' of the head portion. The lug in the slot thus defines a pivot point for each arm 29, 29', while at the same time allowing for some lateral movement of the head 28, 28'.

Each head of each arm has a nose portion 32, 32' which locates under an inclined surface 33, 33' of the associated jaw member. The part 34, 34' of the head opposite to the nose 32, 32' abuts against the shoulder 25, 25' of the cavity of the head portion 21 of the actuator. It will be appreciated that when the two arms are pressed together, the heads 28, 28' of the arms will rotate in the slots 27, 27', and the noses 32, 32' of the heads of the arms will travel along the inclined surfaces 33, 33' of the jaw members. In the second position of the arms, shown in FIG. 6, the distance from the lugs 31, 31' to the inside faces of the jaw members 23, 23' is significantly greater than in the first position, shown in Fig.3, because in the second position the heads 28, 28' of the arms 29, 29' contact the jaw members 23, 23' across the length of the noses 32, 32' and because the noses 32, 32' contact the jaw members 23, 23' closer to the point of greatest width of the jaw members. Thus, on closing of the arms, the jaw members are urged together.

It should further be noted that the shoulders 25, 25' of the cavity also have inclined surfaces and that the parts 34, 34' of the heads 28, 28' are shaped like the noses 32, 32' so that, upon rotation, the heads 28, 28' of the arms are urged inwardly, with the lugs 31, 31' moving along the slots 27, 27', as the parts 34, 34' move along the inclined surfaces of the shoulders 25, 25'.

It will be understood that other forms of cam arrangements can be employed between the arms 29, 29' and the jaw members 23, 23' so that the pivoting of the arms towards each other is translated into a squeezing together of the jaw members with a high relatively high force.

To use the actuator device of FIGS. 5 and 6, a filled container, or a filled container 1 plus nozzle 10, is slotted in between the jaw members in their open position. The arm members are then squeezed together, into the position shown in FIG. 6, thereby squeezing the jaw members together to compress the container, burst the container and expel the contents through the discharge outlet or nozzle.

It will also be appreciated that the arm members themselves could act directly on the container, rather than through the jaw members. However, it is believed that better control of the bursting of the container is achieved with the intermediate jaw members of the described embodiment.

Figure 7:
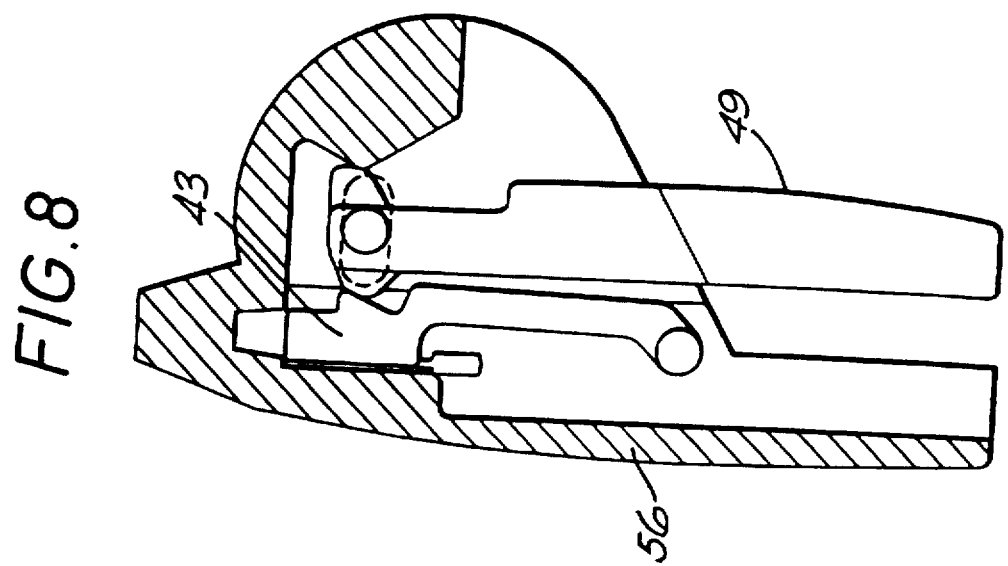
FIGS. 7 and 8 are sectional views of a second embodiment of the administering device according to the invention showing the device prior to discharge of the contents of the container and after discharge respectively.
Figure 8:
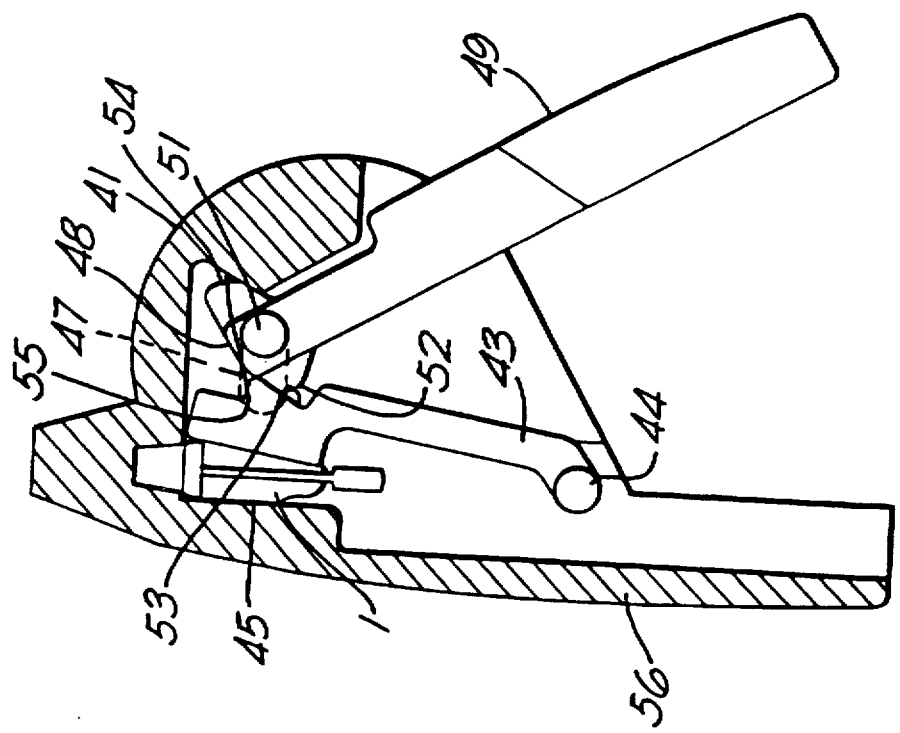

The second embodiment of the actuator, shown in FIGS. 7 and 8, is similar to the first embodiment except it can be characterised as having only one movable jaw member 43 and one movable arm member 49. Thus, the container 1 is supported between an internal wall 45 of the cavity of the head portion 41 of the actuator and the face of one jaw member 43. The jaw member 43 pivots about a pivot point 44. A single movable arm 49 extends out of the cavity of the head portion 41, a lug 51 on the head 48 of the arm 49 being fitted in an elongate slot 47 of the actuator.

As in the first embodiment, a nose 52 of the head 48 of the arm 49 abuts an inclined surface 53 of the jaw member and an opposing part 54 of the head of the arm abuts an inwardly inclined shoulder 55 of the cavity of the head portion of the actuator.

The side of the actuator on which the container is supported is extended to form a handle portion 56. On pressing together of the arm 49 and the handle portion 56, the head 48 of the arm pivots in the slot 47, the nose 52 and opposing part 54 move along the inclined surfaces 53, 55 and the jaw member 43 is urged towards the inner face 45 of the cavity, thereby compressing the container 1. The closed position of the member is shown in FIG. 8.

Figure 9:
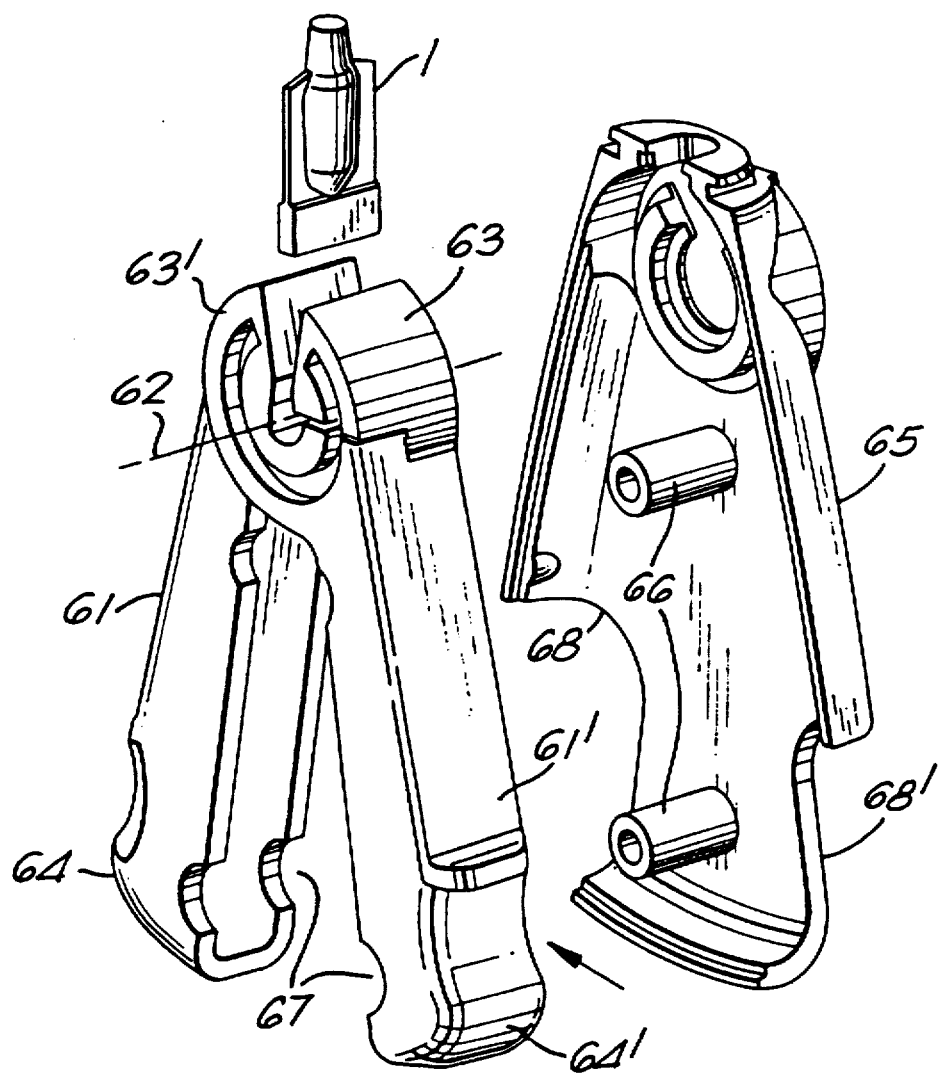
FIG. 9 is a perspective exploded view of a third embodiment of an administering device according to the invention.

In the exploded view of FIG. 9, the actuator is seen along with the container 1 and the end cap 12, plug 13 and body 11 of the nozzle 10.

The actuator comprises a pair of members 61, 61' which are hinged together, the members crossing each other at the hinge axis 62 in the manner of a pair of pliers or a pair of scissors. Each movable member consists of a head portion 63, 63' and an arm portion 64, 64'. Thus, when squeezing together the arm portions 64, 64', the head portions 63, 63' are also squeezed together.

The movable members 61, 61' are fitted into a cover 65, one half of which is seen in the figure. Circular lugs 66 on one half of the cover locate in opposing semi-circular recesses 67 on the insides of the arms 64,64', when the arms are closed together.

After the pair of movable members is fitted on the one half of the cover, the combination of the container 1 and nozzle 10 is slotted in between the head portions 63, 63', with the nozzle 10 extending out of the cover. The other half of the cover is then fitted on to form the complete actuating device.

The cover 65 has cut-away portions 68, 68' on opposite sides thereof so that the ends of the arm portions 64, 64' are accessible to the user when fitted into the cover.

To use the device, the arm portions 64, 64' are simply pressed together, thereby pressing the head portions 63, 63' together to burst the container 1, the contents of which are expelled through the nozzle 10.

The used container/nozzle unit is then removed and discarded. To re-use the actuator, a fresh container/nozzle unit is slotted in.

The fourth embodiment of the actuator, shown in FIG. 10, is similar to the first embodiment in that it has two moveable arms acting on a pair of jaw members with intervening cam surfaces. However, this embodiment differs from the earlier embodiments in that the force which moves the arms together is provided by a spring, rather than manually.

The heads 88, 88' of the arm members 89, 89' and the jaw members 83, 83' are substantially the same as those of the first embodiment illustrated in FIGS. 5 and 6, and so are not described again. At the end of each arm 89, 89' is a ledge 90, 90' which defines a seat for one end of a C-spring 91. The spring 91 is under tension so that it tends to urge the arms 89, 89' together.

In the position shown in FIG. 10, the arms 89, 89' are maintained in a separated position by a catch (not shown). This catch can be released by pressing a trigger (again not shown). On release of the catch, the spring 91 forces the arms 89, 89' together, thereby rotating their heads 88, 88' to close the jaw members 83, 83' and bursting the container.

Because the arms 89, 89' do not need to be manipulated by the user they can be concealed within the actuator body. For a disposable actuator, the spring is primed on manufacture of the device and is intended to be released only once, after which the actuator is thrown away.

The advantage of the arms being moved by a spring force, rather than manually, is that the force exerted on the container is substantially constant for all users. This means that the spray pattern from the container is constant, which provides for better delivery of the pharmaceutical substance.

The actuator of FIG. 11 also uses a spring force to move the arms, although in this embodiment the arms are moved apart rather than together. Thus between the arms 109, 109' is fitted a torsion spring 111 with its ends extending as torsion bars 112, 112', one being attached to one arm 109 and the other being attached to the other arm 109'. The arms are held in a position adjacent to each other by means of a catch (not shown). Upon release of the catch, the spring 111 forces the arms apart, thereby closing the jaw members 103, 103' to burst the container 1.

It should be noted that because the arms are moved apart, rather than together, the heads 108, 108' of the arms are rotated in an opposite sense to that of the previous embodiment. The arrangement of the cooperating surfaces of the heads 108, 108', the jaw members 103, 103' and the actuator body is thus correspondingly different.

Figure 12:
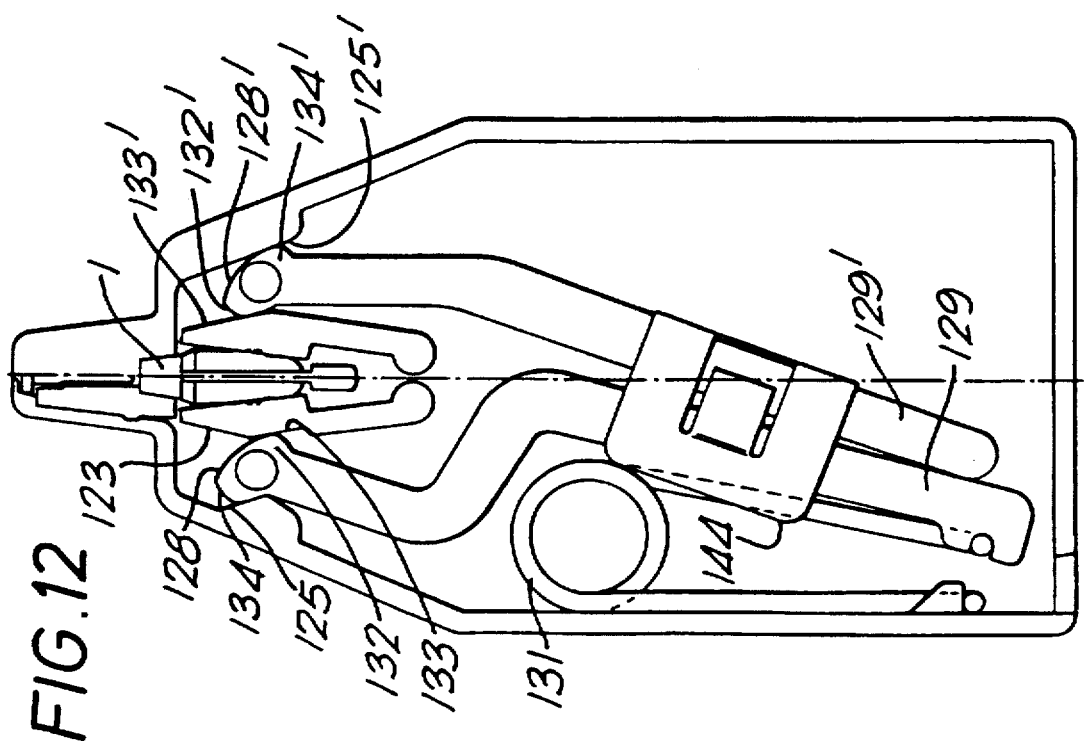
FIG. 12 is a sectional view of a sixth embodiment of an administering device according to the invention.

The actuator of FIG. 12 also uses a torsion spring but in this embodiment the spring 131 is fitted between the side of the actuator body and one of the arms 129, 129', the arms being connected together by a clip 144. The linking of the arms together allows the size of the actuator to be minimized.

Because the arms 129, 129' are connected, the heads 128, 128' rotate in the same sense, when the arms move. Thus, unlike the earlier embodiments, the arrangements of the cooperating surfaces are not symmetrical about the container 1. The left hand head 128 in FIG. 12 has a nose 132 which locates beneath an upwardly and outwardly inclined surface 133 of the jaw member 123. The back portion 134 of the head 128 locates above an inwardly and downwardly inclined surface 125 on the inside of the actuator body. This arrangement is similar to that seen in FIGS. 5 and 10.

In contrast, the right hand head 128' in FIG. 12 has a nose 132' which locates above a downwardly and outwardly inclined surface 133' of jaw member 123', while the back portion 134' locates against an upwardly and inwardly inclined surface 125' on the inside of the actuator. This latter arrangement is similar to that of FIG. 11.

With this arrangement the pivot points of the arms 129, 129' may be floating and controlled solely by the force exerted on the heads 128, 128' by the surfaces 133, 133' of the jaw members and surfaces 125, 125' of the actuator body. Thus, the lugs and slots of the earlier embodiments are not required here to define the pivot points for the arms 129, 129'.

Upon release of the spring 131, the arms 129, 129' both move rightwardly, the heads 128, 128' both rotate anti-clockwise and each forces one jaw member 123 or 123' inwards to burst the container.

It can be mentioned at this point that the actuator of FIG. 12 can be reusable. For this purpose, a supply of container/nozzle units as shown in FIGS. 4a and 4b can be supplied to the user. After one actuation, the unit is pulled out from the actuator and a fresh one is pushed in. It will be understood that the jaw members 123, 123' slot into the gap between the legs 12A so as to abut the container 1.

Figure 13:
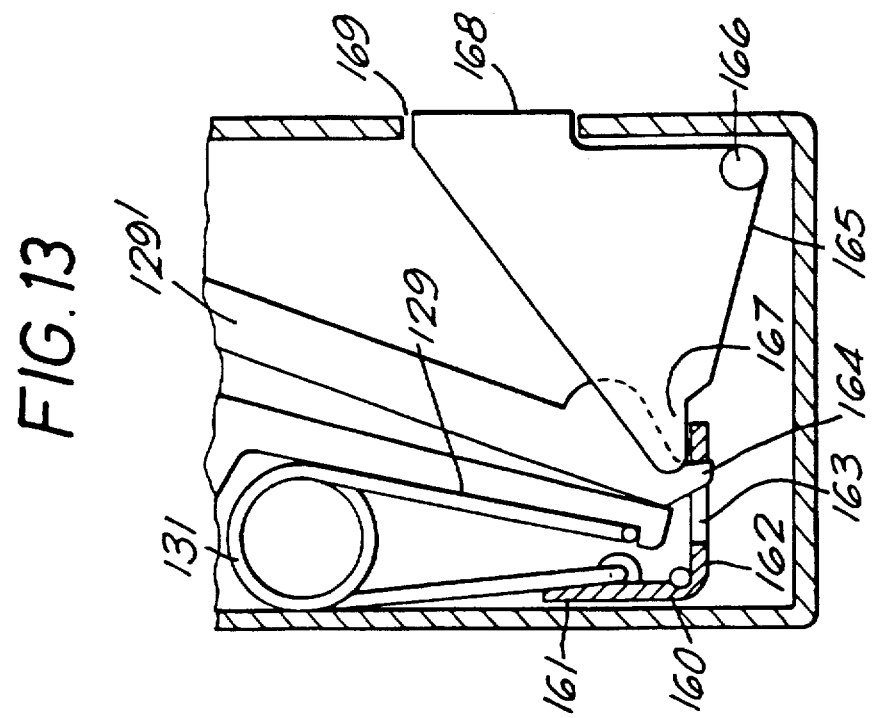
FIG. 13 is a detailed sectional view of a trigger mechanism for the device of FIG. 12.

FIG. 13 shows a trigger mechanism for releasing the spring of the actuator of FIG. 12. An L-shaped catch member 160 is mounted inside the actuator body, one leg 161 of the member being fitted against the side of the body and the other 162 extending into the middle of the body and having an aperture 163 for receiving a lip 164 on the end of the arm 129'. The member 160 is either formed of resilient material or is allowed to pivot.

Trigger member 165 pivots about axis 166 on the opposite side of the actuator body to the catch member 160. The member 165 is formed of a pair of parallel substantially triangular plates which define between them a gap within which the arms 129, 129' can move. One corner 167 of each plate rests on top of the catch member 160. The plates of the member 165 are joined by a web 168 which forms a button and is located in an aperture 169 in the side of the actuator body. Upon pressing of the button 168, the member 165 is pivoted downwardly, thereby lowering the catch member 160 and releasing the arms 129,129'.

For the actuator device to be reusable, some mechanism for repriming the spring should also be provided. For the embodiment of FIG. 12, this could conveniently be provided by a priming boss or spike cooperating with an aperture in the base of actuator body. The priming spike could, if desired, be formed at the bottom of a carrying case for the actuator. Upon pressing of the actuator onto the priming spike, it slides upwardly into the actuator body, thereby forcing the arms 129, 129' to the left as seen in FIG. 12—until the arm 129' engages on the catch member 160 (FIG. 13). It can be noted that such a priming spike is described in more detail below, with reference to FIGS. 19 to 21.

Figure 14A:
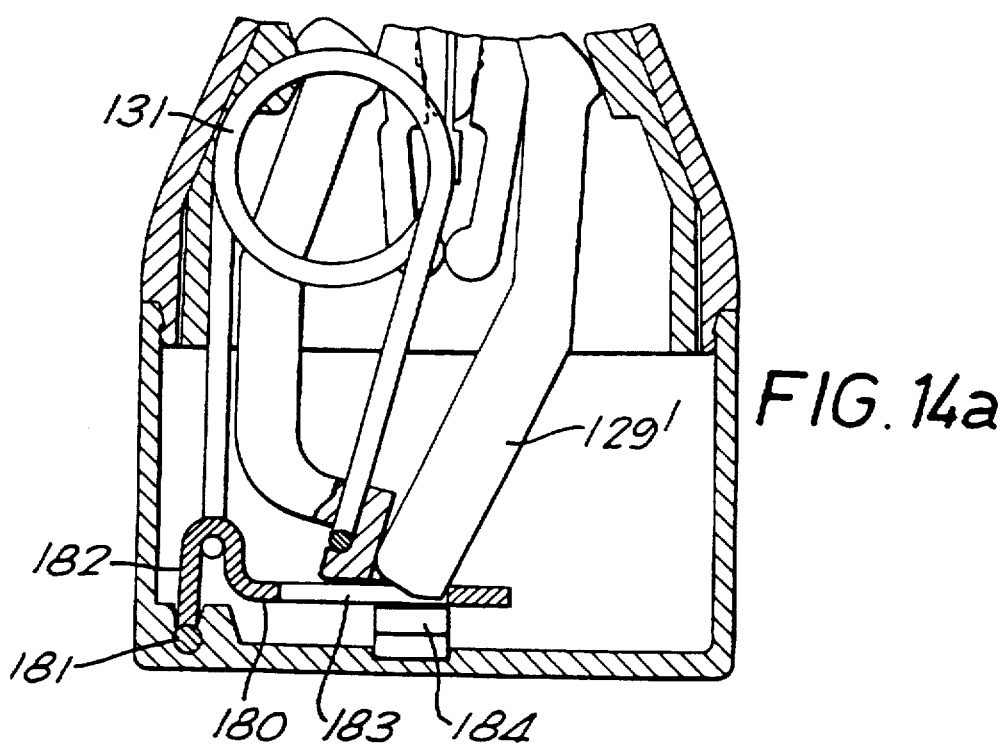
FIGS. 14a, 14b, 15a and 15b are detailed sectional views of another trigger mechanism for an administering device similar to that of FIG. 12.
Figure 14B:
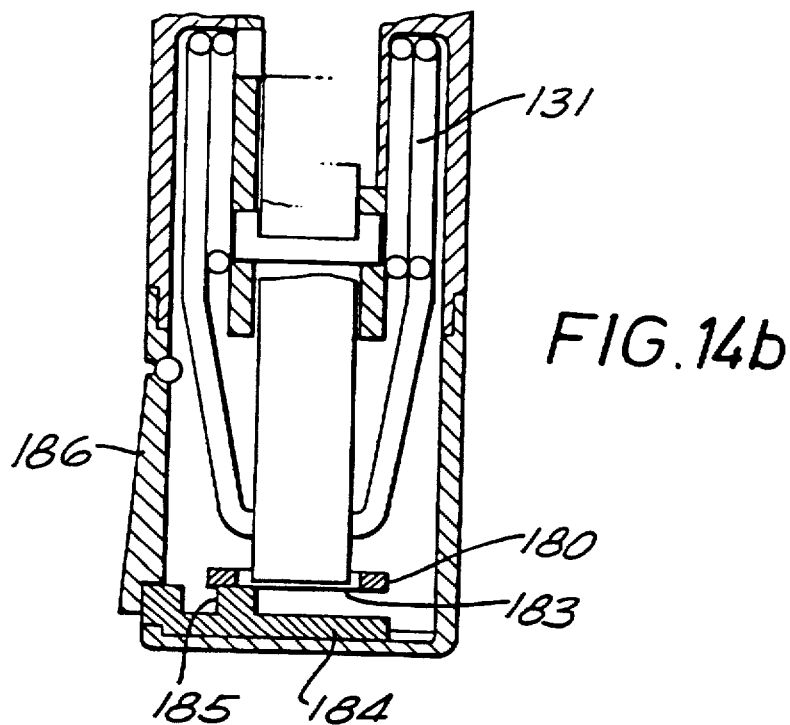
Figure 15A:
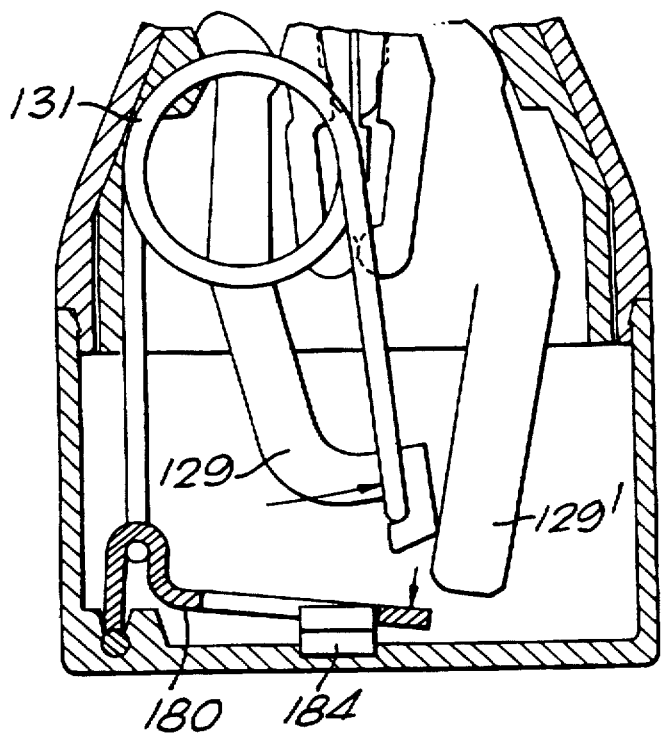
Figure 15B:
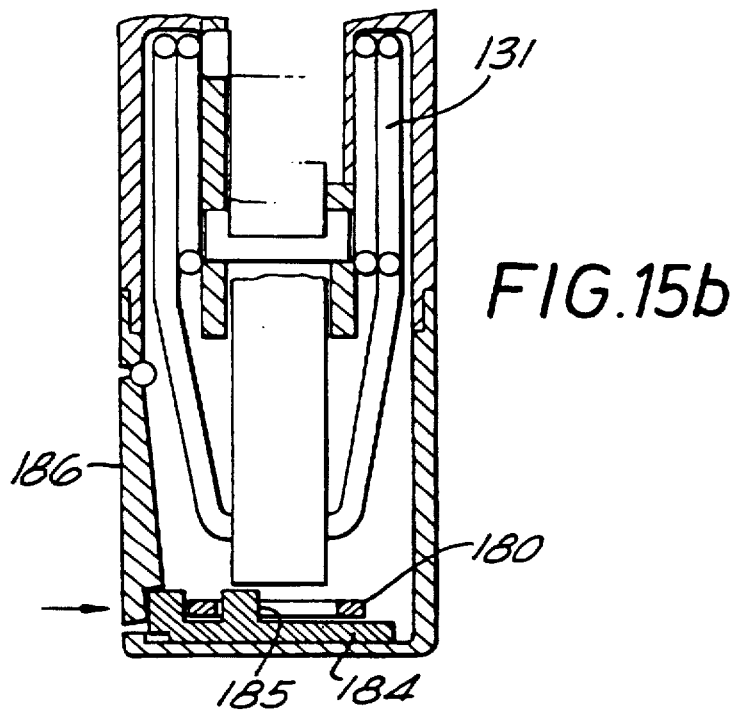

FIGS. 14 and 15 show another trigger mechanism for an actuator similar to that shown in FIG. 12. FIGS. 14a and 15a are sectional views showing the spring in a primed and released position respectively and FIGS. 14b and 15b are sectional views, taken at right angles to the views of the FIGS. 14a and 15a, again showing the spring primed and released.

Catch member 180 is pivoted on the actuator body at 181 and has a hooked portion 182 in which is fitted one end of the spring 131. The catch 180 has an aperture 183 in which the end of arm 129' locates. It should be noted that due to the angle of inclination of the surface of the end of the arm 129' in the aperture, if the catch 180 is able to move downwards, the arms 129, 129' would immediately be released by the spring force.

As most clearly seen in FIG. 14b, the catch 180 is kept in a position in which the arm 129' is restrained by a sliding stop 184. A step 185 on the stop 184 engages beneath the part of the catch 180 surrounding the aperture 183. It will be readily understood that when the stop 184 is moved to the right in FIG. 14b, the catch will be forced downwards by the spring force acting on the hooked portion 182 and the arms 129, 129', with the aperture 183 slotting over the step 185.

FIG. 14b also shows a trigger plate 186 mounted on the side of the actuator body, the upper end of the plate being pivotally connected to the actuator body and the lower end being in engagement with the sliding stop 184. Pressing of the trigger plate 186 thus releases the arms 129, 129' so that the jaw members 123, 123' are closed and the container is burst.

The released position of the catch member 180 and the arms is seen in FIGS. 15a and 15b.

Figure 17B:
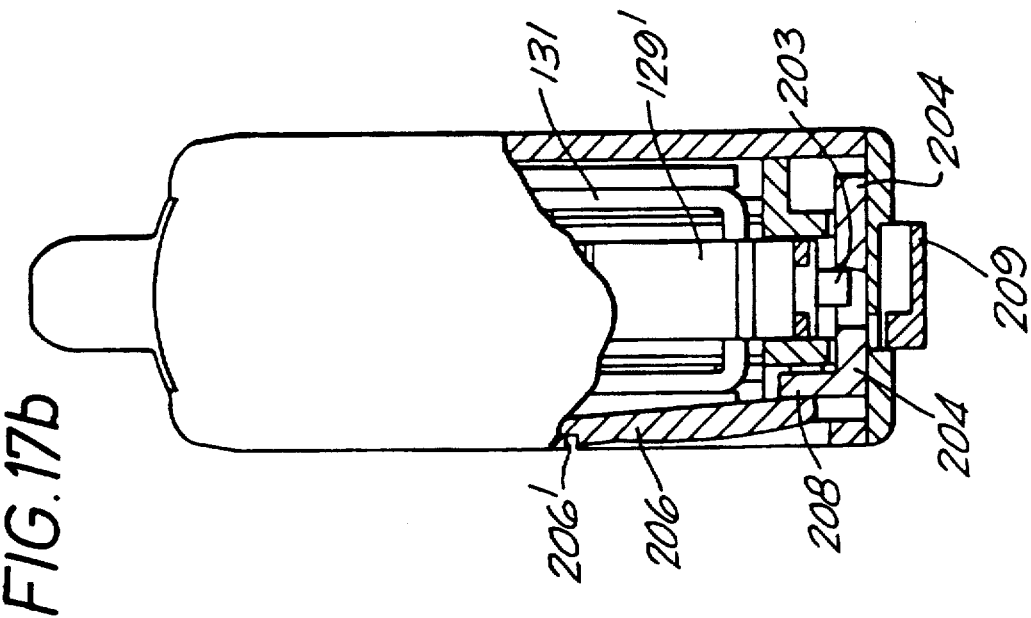
Figure 17A:
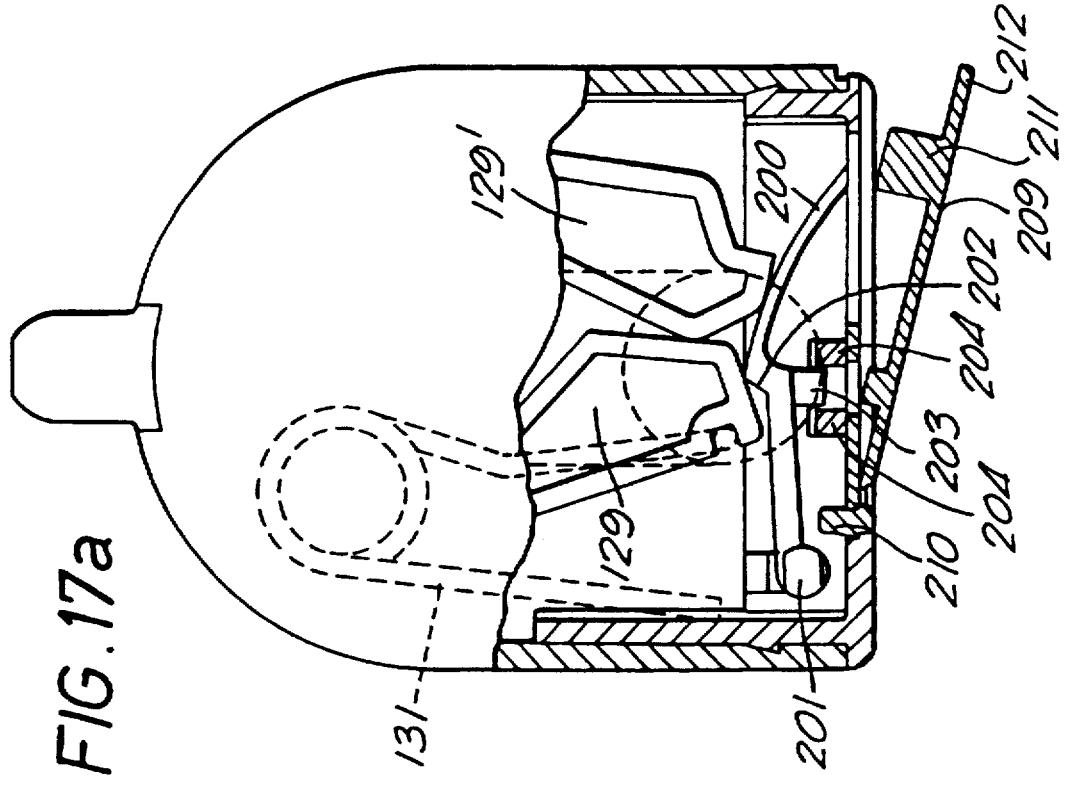
Figure 18:
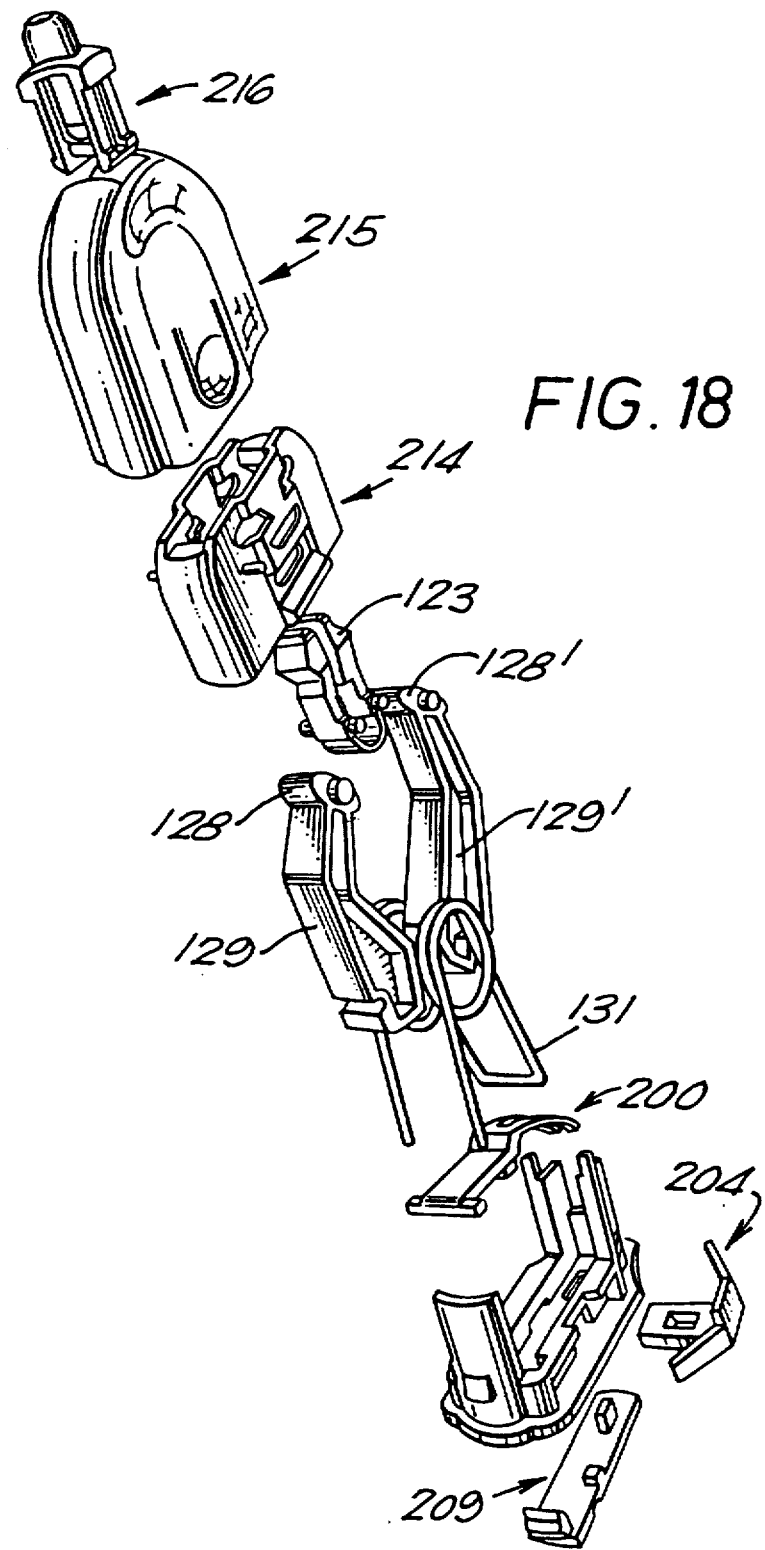
FIG. 18 is a perspective exploded view of the embodiment shown in FIGS. 16 and 17.

FIGS. 16, 17 and 18 show an actuator similar to that shown in FIGS. 14 and 15 but with a different trigger mechanism. FIGS. 16a and 17a are sectional views showing the spring in a primed and released position respectively and FIGS. 16b and 17b are sectional views taken at right angles to the views of FIGS. 16a and 17a, again showing the spring primed and released. FIG. 18 is an exploded view showing all the components of the actuator.

In the actuator of FIGS. 16, 17 and 18, the trigger plate is on the front of the device, rather than the side. In addition, a safety mechanism is provided to ensure that accidental actuation does not occur.

As seen in FIGS. 16a and 16b, the end of arm 129' is engaged behind step 202 of catch member 200. Catch member 200 is pivoted on the actuator body at 201 and prevented from moving down by engagement of block 203 with sliding stop 204. The sliding stop extends at right angles to the plane in which the arms 129, 129' move and is formed with a recess 207 of a size to allow block 203 to move into it when the sliding stop is moved to the right in FIGS. 16b and 17b.

The sliding stop 204 is abutted by trigger plate 206 on the front of the actuator. The trigger plate is formed by moulding the front of the actuator with a substantially U-shaped break line and a line 206' of reduced thickness across the top of the "U".

Accidental movement of the sliding stop 204 is prevented by a safely latch 209 which is clipped onto the base of the actuator body. One end 210 of the latch 209 is fixedly clipped to the base whereas the other end 211 is releasably clipped to the base. The safety latch is made of a resilient material to allow bending of one end with respect to the other. The second end 211 of the latch 209 has a lip 212 which extends beyond the edge of the actuator body so that it is accessible to the user.

As most clearly seen in FIG. 16b, the safety latch 209 engages in recess 207 in the sliding stop 204 so preventing its movement. When the user wishes to actuate the device, the lip 212 is pushed downwards, thus releasing end 211 of the safety latch and moving the safety latch out of engagement with the sliding stop 204.

When the trigger plate 206 is now pressed, it pivots slightly about the line of reduced thickness 206' and pushes the sliding stop 204 to the right in FIGS. 16b and 17b, i.e. to the rear of the device. This allows catch member 200 to move downwards under the action of spring 131 acting through arms 129, 129' and releases the engagement of the arm 129' with the step 202 and so the container is compressed and burst as previously described.

The released positions of the arms 129, 129' and also of the safety latch 209 are seen in FIGS. 17a and 17b.

For the purposes of manufacture of the actuator it has been found to be convenient to incorporate a chassis member 214, as shown in FIG. 18, that fits as a sleeve within the housing 215. The use of a chassis member 214 allows the components to be easily moulded and "snap-fitted" together. The chassis member also provides internal inclined surfaces against which the heads 128, 128' locate.

FIGS. 19, 20 and 21 show an actuator which is similar to that of FIGS. 16, 17 and 18. Views 19a and 19b and 20a and 20b and 21 correspond to the views 16a and 16b and 17a and 17b and 18 respectively. Corresponding parts in FIGS. 19, 20 and 21 are given the same reference numerals as in FIGS. 16, 17 and 18.

The main difference between the actuator of FIGS. 19, 20 and 21 and that of FIGS. 16, 17 and 18 is that the actuator of FIGS. 19, 20 and 21 is intended to be reusable. Thus, the container/nozzle unit 216 as shown in FIG. 21 can be replaced and the combination of the spring 131 and arms 129, 129' can be reprimed. Incidentally, when the container/nozzle unit is inserted into the actuator, the jaw members 123 (shown in FIG. 21) exert a force of approximately 1 kgf on the container. In other words, the container is precompressed in the actuator. This reduces the amount of travel required of the jaw members and hence the overall size of the device.

Another difference between the two actuators is that the actuator of FIGS. 19, 20 and 21 does not include the safety latch shown in FIGS. 16, 17 and 18, although a corresponding safety catch can be provided to prevent accidental actuation.

As seen in the figures, the arm 129' is held in a primed position by step 202 of catch member 200. Step 208 is abutted by trigger plate 206 on the front of the actuator. The shape and position of the trigger plate is indicated by the dotted lines in Fig. 19a and 20a. The sliding stop 204 has an integral spring action which urges it to the right in FIGS. 19b and 20b, i.e. against the inward movement of the trigger plate 206. The catch member 200 is provided with two separate parallel legs 213, and an integral spring action urges the catch member 200 upwards against engagement area of arm 129'.

An aperture 220 is formed in the base of the actuator body, adjacent the position of the sliding stop 204 and in alignment with a gap between the two parallel legs 213. This aperture 220 is to allow insertion of a priming spike 221, as seen in FIGS. 19a and 20a. FIG. 19a shows the spike 221 in a fully inserted position. The spike 221 has an inclined face 222 which abuts the side of the arm 129'. It will be understood that upon pressing the released actuator onto the spike 221, the arm 129' rides over legs 213 to push the catch member 200 down whilst the arms 129, 129' are moved from the position seen in FIG. 20a until the catch member 200 and sliding stop 204 spring back to the positions seen in FIG. 19a, i.e. the position in which the arm 129' is engaged behind the step 202 of the catch member 200.

Release of the arms 129, 129' by pressing the trigger plate 206 is as described in relation to FIGS. 16 and 17.

Once the arms have been released and the container burst it is not possible to replace the container/nozzle unit until the spring 131 and arms 129, 129' have been reprimed such that minimal jaw force is applied to the container wall.

As can be seen in FIG. 21 the container/nozzle unit 216 may be held tightly in place by ledges 217 at the base of the nozzle legs fitting into slots 218 within the chassis member 214. Nozzle shuttles 219 are provided between the chassis member 214 and housing 215 and present abutment surfaces which cooperate with slots 218. The nozzle shutters 219 are accessible through holes 220 in the housing 215. To disengage ledges 217 from slots 218 the nozzle shuttles 219 are depressed through holes 220. The abutment surfaces of the nozzle shuttles 219 move into the slots 218 and push the nozzle legs until the ledges 217 are released from engagement with slots 218 allowing the container/nozzle unit 216 to be removed by hand.

FIG. 22 is an exploded view of the actuator carry case. When assembled, wings 301 snap-fit onto the priming spike moulding 302 which itself snap-fits into base 303. Lid 304 is attached by pivot pins 305 to the pivot axis on the priming spike moulding.

The carry case provides a convenient storage system for the reloadable actuator illustrated in FIGS. 19, 20 and 21. The actuator may be stored without nozzles in place in the profiled region closest to the pivot where the priming spike 221 is located. The remainder of carry case space is used to store container/nozzle units.

The carry case also acts as a means for reloading the actuator. This is done by placing the actuator into the profiled region of the carry case closest to the pivot point. The actuator will be resting on the carry case spike 221 with the spike partially inserted as shown in FIG. 20a. The lid 304 of the carry case can now be lowered to act as a lever to force the actuator down against the spike 221 to reprime the device. The carry case lid 304 is almost fully closed when the actuator is finally primed. With the reprimed actuator still in place in the carry case the inside surfaces of the wings 301 are aligned with the nozzle release shuttles 219. The container/nozzle unit 216 can now be removed by opening the carry case lid 304 and depressing the wings 301 of the carry case. The inside surface of the wings 301 abut against the nozzle release shuttles 219 to allow removal of the container/nozzle unit as described above. The carry case lid can only be fully closed with an actuator in place when the nozzle has been removed.

It is claimed:

1. A device for administering pharmaceutical substances by spraying the contents of a container formed of plastics material, the device comprising a pair of members for supporting the container therebetween, and a discharge outlet, wherein when the container is present one or both members are movable between a first position in which the container is not compressed sufficiently to burst it and a second position in which the members are capable of exerting sufficient pressure on the container to burst it, thereby expelling the contents through the discharge outlet, wherein the one or both members are movable by means of one or a pair of handle members, and a means is interposed between the one or both movable members and the one or both handle members for magnifying the force applied to the one or both handle members, and a cam mechanism is interposed between the one or both movable members and the one or both handle members.

2. A device according to claim 1, wherein the two members are pivotally movable relative to each other.

3. A device according to claim 1 incorporating a plastics container for containing the pharmaceutical substance to be sprayed.

4. A device according to claim 3, wherein the plastics container has a predetermined point of rupture.

5. A device according to claim 4, wherein the predetermined point of rupture is defined by an area of the container having a thickness which is substantially less than the other walls of the container.

6. A device according to claim 4, wherein the predetermined point of rupture is defined by a point or line of weakness.

7. A device according to claim 4, wherein the container will rupture when the contents of the container reaches a predetermined pressure.

8. A device according to claim 1, wherein the discharge outlet serves to channel the spray from the container out of the device.

9. A device according to claim 8, wherein the discharge outlet is a spray nozzle.

10. A device according to claim 8, wherein the discharge outlet is assembled as a unit with the container.

11. A device according to claim 1 wherein the one or both handle members are adapted to be squeezed together by the user's hand.

12. A device according to claim 1 wherein a spring and trigger mechanism are connected to the members supporting the container such that the members are urged together upon release of the spring force by the trigger mechanism.

13. A device according to claim 12 wherein the spring and trigger mechanism may be re-set and the container replaced after actuation of the device.

14. A device according to claim 1, wherein the pharmaceutical substance is for the treatment of influenza, migraine, respiratory diseases or allergic rhinitis.

15. A device according to claim 14, wherein the pharmaceutical substance is 4-Guanidino-Neu5Ac2en.

16. A device according to claim 14, wherein the pharmaceutical substance is sumatriptan.

17. A combination of a device according to claim 13 and a housing for the device and at least one container of the pharmaceutical substance to be discharged.

18. A combination according to claim 17, wherein the housing has a lid which may be closed after the device is returned thereto.

19. A combination according to claim 17, wherein the housing includes means to re-set the spring and trigger mechanism when the device is placed into the housing.

20. A method of administering pharmaceutical substances by means of the device of claim 1 by spraying the contents of the container formed of plastics material by applying sufficient pressure to the container to burst it and expel the contents through the discharge outlet.

21. A method according to claim 20, wherein the plastics container has a predetermined point of rupture.

22. A method according to claim 21, wherein the predetermined point of rupture is defined by an area of the container having a thickness which is substantially less than the other walls of the container.

23. A method according to claim 21, wherein the predetermined point of rupture is defined by a point or line of weakness.

24. A method according to claim 21, wherein the container will rupture when the contents of the container reaches a predetermined pressure.

* * * * *